United States Patent
Ono et al.

(10) Patent No.: US 8,017,732 B2
(45) Date of Patent: Sep. 13, 2011

(54) TUMOR MARKER FOR PANCREATIC CANCER

(75) Inventors: Masaya Ono, Tokyo-To (JP); Tesshi Yamada, Tokyo-To (JP); Setsuo Hirohashi, Tokyo-To (JP)

(73) Assignee: Japan Health Sciences Foundation, Tokyo-To (JP)

( * ) Notice: Subject to any disclaimer, the term of this patent is extended or adjusted under 35 U.S.C. 154(b) by 15 days.

(21) Appl. No.: 12/452,824

(22) PCT Filed: Jul. 24, 2008

(86) PCT No.: PCT/JP2008/063235
§ 371 (c)(1),
(2), (4) Date: Feb. 24, 2010

(87) PCT Pub. No.: WO2009/014160
PCT Pub. Date: Jan. 29, 2009

(65) Prior Publication Data
US 2011/0112278 A1    May 12, 2011

(30) Foreign Application Priority Data
Jul. 25, 2007    (JP) ................................. 2007-193328

(51) Int. Cl.
*C07K 2/00*    (2006.01)
*C07K 14/47*    (2006.01)
(52) U.S. Cl. ....................................... 530/350; 530/300
(58) Field of Classification Search .................... None
See application file for complete search history.

(56) References Cited

FOREIGN PATENT DOCUMENTS
WO    2006/125021    11/2006

OTHER PUBLICATIONS

Supplementary European Search Report dated Jul. 30, 2010 in Application No. EP 08 79 1487.

J. Koopmann et al., "Serum Diagnosis of Pancreatic Adenocarcinoma Using Surface-Enhanced Laser Desorption and Ionization Mass Spectrometry", Clinical Cancer Research, vol. 10, No. 3, pp. 860-868, Feb. 1, 2004.
C. Rosty et al., "Identification of Hepatocarcinoma-Intestine-Pancreas/Pancreatitis-Associated Protein I as a Biomarker for Pancreatic Ductal Adenocarcinoma by Protein Biochip Technology", Cancer Research, vol. 62, No. 2, pp. 1868-1875, Mar. 15, 2002.
International Search Report issued Sep. 16, 2008 in International (PCT) Application No. PCT/JP2008/063235.
M. Bloomston et al., "Fibrinogenγ Overexpression in Pancreatic Cancer Identified by Large-scale Proteomic Analysis of Serum Samples", Cancer Research, vol. 66, No. 5, pp. 2592-2599, Mar. 1, 2006.
J. M. Radhi et al., "Pancreatic Cancer and Fibrinogen Storage Disease", J. Clin. Pathol., vol. 51, pp. 865-867, 1998.
V. Abbasciano et al., "Coagulation Disorders and Tumor Markers in the Diagnosis of Pancreatic Cancer", Oncology, vol. 48, pp. 377-382, 1991.
S. A. Maxwell et al., "Proline Oxidase Induces Apoptosis in Tumor Cells, and its Expression is Frequently Absent or Reduced in Renal Carcinomas", The Journal of Biological Chemistry, vol. 278, No. 11, pp. 9784-9789, Mar. 14, 2003.
J. Pandhare et al., "Proline Oxidase, a Proapoptotic Gene, is Induced by Troglitzone", The Journal of Biological Chemistry, vol. 281, No. 4, pp. 2044-2052, Jan. 27, 2006.
K. Honda et al., "Suizo Soki Hakken no Shin Gijutsu", Japanese Journal of Clinical Medicine, vol. 64, No. 9, pp. 1745-1755, 2006.
M. Maekawa, "Shinki Shuyo Marker ni yoru Suigan Soki Shindan no Kanosei", Igaku no Ayumi, vol. 222, No. 1, pp. 45-50, Jul. 7, 2007.

*Primary Examiner* — Nashaat Nashed
(74) *Attorney, Agent, or Firm* — Wenderoth, Lind & Ponack, L.L.P.

(57) ABSTRACT

A novel protein and a fragment thereof useful as a tumor marker of pancreatic cancer are disclosed. This protein or a fragment thereof is a modified α-fibrinogen protein containing an oxidized amino acid residue(s) or a fragment thereof containing said oxidized amino acid residue(s). The oxidized amino acid residue(s) is one or more amino acid residues selected from the group consisting of (a) a proline residue corresponding to the proline residue at the position of 530 in SEQ ID NO: 2, and (b) a proline residue corresponding to the proline residue at the position of 565 in SEQ ID NO: 2.

9 Claims, 9 Drawing Sheets

TUMOR MARKER FOR PANCREATIC CANCER

This application is a U.S. national stage of International Application No. PCT/JP2008/063235 filed Jul. 24, 2008.

CROSS-REFERENCE OF RELATED APPLICATION

This patent application claims a priority based on a prior Japanese Patent Application, Japanese Patent Application No. 193328/2007 (filing date: Jul. 25, 2007). The whole disclosure of Japanese Patent Application No. 193328/2007 is incorporated herein by reference.

BACKGROUND OF THE INVENTION

1. Field of the Invention

The present invention relates to a novel protein and fragment thereof which can be used as a tumor marker in the diagnosis of pancreatic cancer as well as a process for diagnosing pancreatic cancer with use of the marker.

2. Background Art

It is known that pancreatic cancer is a cancer which originates in pancreas, and 90% or more of the cancer is pancreatic duct adenocarcinoma originating in the exocrine cells, particularly the cells of the pancreatic duct, through which pancreatic juice is transferred. It is very difficult to find pancreatic cancer, because pancreas is surrounded by many organs such as stomach, duodenum, spleen, small intestine, large intestine, liver and gall bladder. On the other hand, pancreatic cancer tends to begin spreading to other organs at its initial stage and thus has an inclination of easy metastasis. Thus, it is essential for the therapy of pancreatic cancer to detect it at its early stage.

In general, tumor markers which enable the diagnosis of cancers by blood test are useful for detection of cancer at its early stage. The tumor markers of pancreatic cancer include, for example, CA19-9, CEA, Dupan-2, and the like. However, it is often difficult to detect pancreatic cancer at its early stage even with these tumor markers. Therefore, there is a demand on the development of novel tumor markers of pancreatic cancer.

Fibrinogen is a glycoprotein which is transferred by blood and consists of three different polypeptide chains. If blood vessel is damaged, fibrinogen is cleaved by thrombin to form fibrin as the main ingredient of clot. In addition, it is known that the cleaved products such as fibrinogen and fibrin are involved with cell adhesion and cell dispersion, exhibit blood vessel contracting activities and chemotactic activities, and also work as mitogenic factors for several cell types. Furthermore, it is known that the plasma concentration of fibrinogen is involved with the risk of coronary diseases (J. Thromb. Haemost. 4(10), 2204-2209, 2006). It is also known that the genetic mutation of α chain of fibrinogen (α-fibrinogen) is involved with disorders such as abnormal fibrinogenemia, fibrinogenopenia, afibrinogenemia and renal amyloidosis (Thromb. Haemost. 96(2), 231-232, 2006; Blood 80(8), 1972-1979, 1992).

SUMMARY OF THE INVENTION

The present inventors have detected a novel α-fibrinogen protein of which a specific amino acid residue is oxidized in a plasma sample of a pancreatic cancer patient, and have found that the concentration of the protein is significantly different between pancreatic cancer patients and normal subjects and thus the protein is useful as a tumor marker of pancreatic cancer. The present invention is based on the above findings.

Thus, the object of the present invention is to provide a novel protein and fragments thereof which are useful as a tumor marker for pancreatic cancer.

The protein and fragments thereof according to the present invention is a modified α-fibrinogen protein containing an oxidized amino acid residue(s) or a fragment thereof containing said oxidized amino acid residue(s), wherein the amino acid residue(s) which is oxidized is one or more amino acid residues selected from the group consisting of (a) a proline residue corresponding to the proline residue at the position of 530 in SEQ ID NO: 2, and (b) a proline residue corresponding to the proline residue at the position of 565 in SEQ ID NO: 2.

According to the present invention, it is possible to detect pancreatic cancer at earlier stages, which has been believed unfeasible, and to develop diagnostic reagents for detecting pancreatic cancer at earlier stages.

DETAILED DESCRIPTION OF THE INVENTION

Figure 1A:
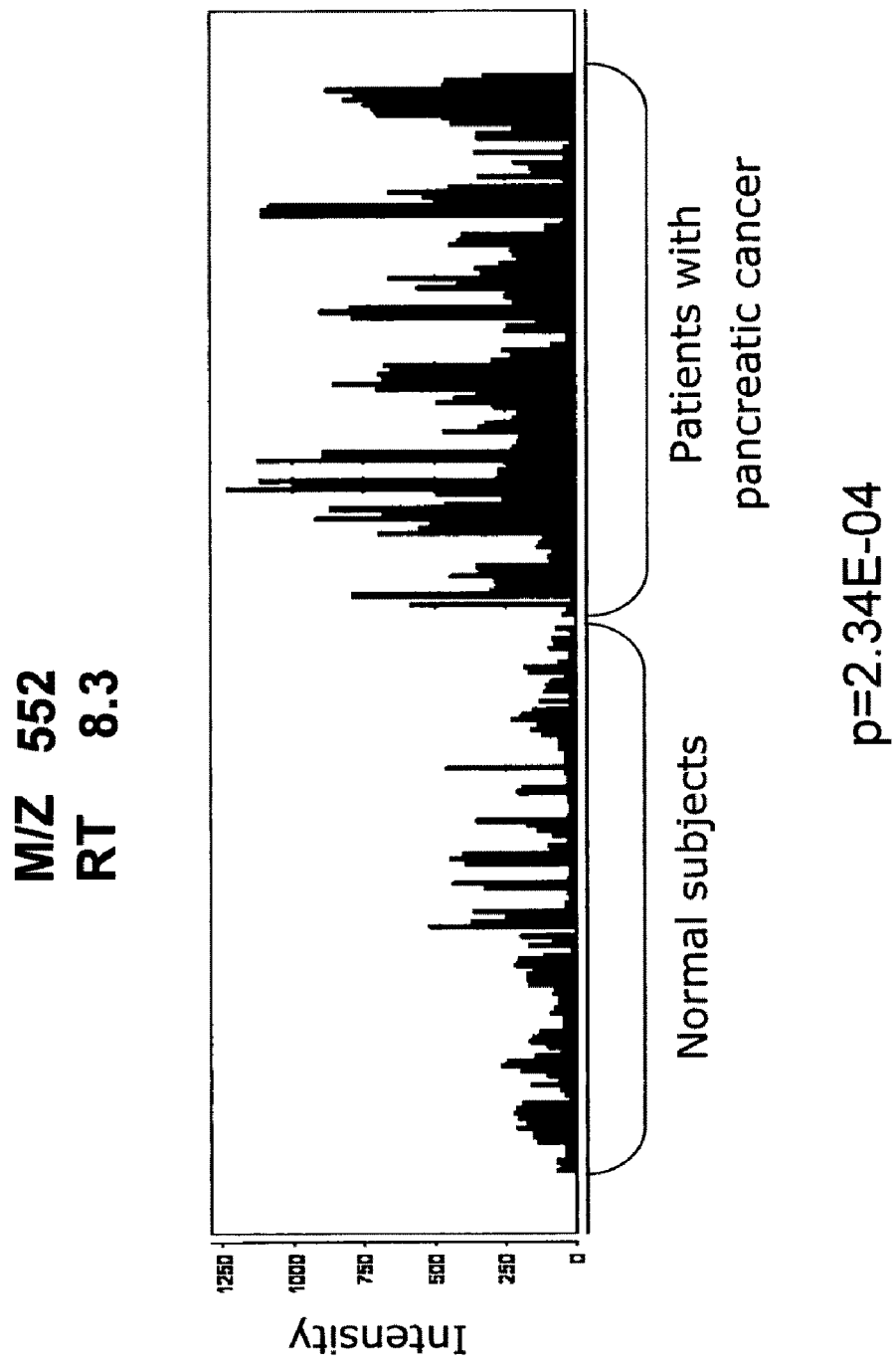
FIG. 1A is a histogram in which intensities of M/Z (mass-to-charge ratio) 552 of a glycoprotein fraction derived from a modified peptide in plasma samples and having a retention time (RT) of 8.3 minutes are compared among a plurality of the LC/MS data.

The term "α-fibrinogen protein" as used herein refers to a chain among the three chains which constitute fibrinogen.

α-fibrinogen protein include a variety of α-fibrinogen proteins derived from a variety of animals and is not limited to any one of them, and is preferably a human α-fibrinogen protein. The human α-fibrinogen protein includes two isoforms obtained by selective splicing, of which the amino acid sequences are illustrated in SEQ ID NO: 2 (NCBI ACCESS NO: NP_068657) and SEQ ID NO: 4 (NCBI ACCESS NO: NP_000499), respectively. In these amino acid sequences, 19 residues at the N terminal is a signal peptide.

In the protein according to the present invention, one or both of (a) the proline residue corresponding to the proline residue at the 530 position in SEQ ID NO: 2 and (b) the proline residue corresponding to the proline residue at the 565 position in SEQ ID NO: 2 are oxidized. The positions of proline residues to be oxidized in a sequence other than SEQ ID NO: 2 may be readily determined by a person skilled in the art, for example, by comparing the sequence with that of SEQ ID NO: 2.

The specific structure of the oxidized amino acid residue may be any of the structures which are known for the partial oxidation of proteins in vivo. Preferred examples of the structures include the ones having an additional oxygen atom as compared with the corresponding natural amino acid residue, more preferably the ones having an additional hydroxy group as compared with the corresponding natural amino acid residue.

In the protein according to the present invention, it is sufficient that either of the amino acid residues described in (a) or (b) may be oxidized, and preferably both of these amino acid residues are oxidized.

In a preferred embodiment of the present invention, the α-fibrinogen protein comprises the residues at 20-644 positions in the amino acid sequence represented by SEQ ID NO: 2, in which either one or both of the proline residues at 530 and 565 positions are oxidized. In a more preferred embodiment, both of the proline residues at 530 and 565 positions are oxidized. In this embodiment, the α-fibrinogen protein may further contain the signal peptide represented by the residues at 1-19 positions in the amino acid sequence of SEQ ID NO: 2.

In another preferred embodiment of the present invention, the α-fibrinogen protein comprises the residues at 20-866 positions in the amino acid sequence represented by SEQ ID NO: 4, and either one or both of the proline residues at positions 530 and 565 in the amino acid sequence are oxidized. In a more preferred embodiment, both of the proline residues at positions 530 and 565 are oxidized. In this embodiment, the α-fibrinogen protein may further contain the signal peptide represented by the residues at 1-19 positions in the amino acid sequence represented by SEQ ID NO: 4.

The protein according to the present invention can be prepared by the conventional methods which are known as the method for preparing proteins. For instance, the cDNA sequence coding for the amino acid sequence represented by SEQ ID NO: 2 is shown in SEQ ID NO: 1 (NCBI ACCESS NO: NM_021871), and the cDNA sequence coding for the amino acid sequence represented by SEQ ID NO: 4 is shown in SEQ ID NO: 3 (NCBI ACCESS NO: NM_000508). A person skilled in the art can construct an appropriate expression vector with reference to these sequences to prepare the protein according to the present invention in an appropriate host cell. The oxidation reaction of the specific amino acid residue can also be carried out by the conventional methods known in the art. Alternatively, the protein according to the present invention may be isolated from plasma samples of pancreatic cancer patients.

The present invention also comprises the fragments of the protein described above. Such fragments contain oxidized amino acid residues described in either one or both of (a) and (b). The fragment of the protein according to the present invention is particularly useful for the development of diagnostic reagents of pancreatic cancer. For example, there may be contemplated as the diagnostic reagent of pancreatic cancer a reagent which is specifically linked to the protein according to the present invention. In order to use the fragment of the protein according to the present invention for developing such reagents, the fragment of the protein according to the present invention is preferably a specific fragment which is specific to the protein according to the present invention. The term "specific" as used herein means that the structure of the fragment is present only in the protein according to the present invention in the reaction system used for the detection of the protein according to the present invention. The sequence and structure of such specific fragments can be determined with a database available in the art. Furthermore, the reagents which are specifically linked to the protein according to the present invention include antibodies, and particularly monoclonal antibodies. In order to use the fragment of the protein according to the present invention for the development of such antibodies, it is preferably an immunogenic fragment which can be used for the preparation of antibodies. The fragment of the protein according to the present invention may be prepared by the methods described above on full-length proteins, or may be prepared by the conventional methods known in the art as the synthetic method of peptides.

The protein according to the present invention and a fragment thereof can be used for the development of diagnostic reagents of pancreatic cancer. Such reagents include those specifically linked to the protein according to the present invention and a fragment thereof, and particularly the reagents are preferably specific antibodies used for ELISA, and the like. Such specific antibodies may be a monoclonal antibody or its binding fragment, ScFv (single stranded Fv fragment), dAb (single domain antibody), or a minimal recognition unit of antibody.

According to one embodiment, said specific antibody may be a monoclonal antibody. The monoclonal antibody can be produced by the standard technique known in the art. By way of example, the methods for producing monoclonal antibodies include the ones described in "Monoclonal Antibodies: A manual of techniques", H. Zola (CRC Press, 1988) and "Monoclonal Hybridoma Antibodies: Techniques and Applications", J. G. R. Hurrell (CRC Press, 1982). Furthermore, non-human antibodies appropriately produced may also be "humanized" by inserting the CDR region of a mouse antibody into the framework of a human antibody. The protein according to the present invention in samples can be correctly detected by using the monoclonal antibody thus produced, and thus pancreatic cancer can be diagnosed rapidly.

EXAMPLE

The present invention is now described in more detail with reference to Example, but is not limited thereto.

Example 1

Identification of a Protein as a Pancreatic Cancer Marker

A 20 μl portion of plasma samples from 43 patients with pancreatic cancer and 43 normal subjects was used for the extraction of glycoprotein fractions adsorbing on concanavalin A. Each of the glycoprotein fractions was analyzed by the 2DICAL method which enables the comparison of the LC/MS data of plural samples (Ono et al., Mol. Cell Proteomics, 5, 1338, 2006). The result of comparison between patients with pancreatic cancer and normal subjects on three peaks derived from a peptide having a modified sequence is shown in FIG. 1.

Figure 1B:
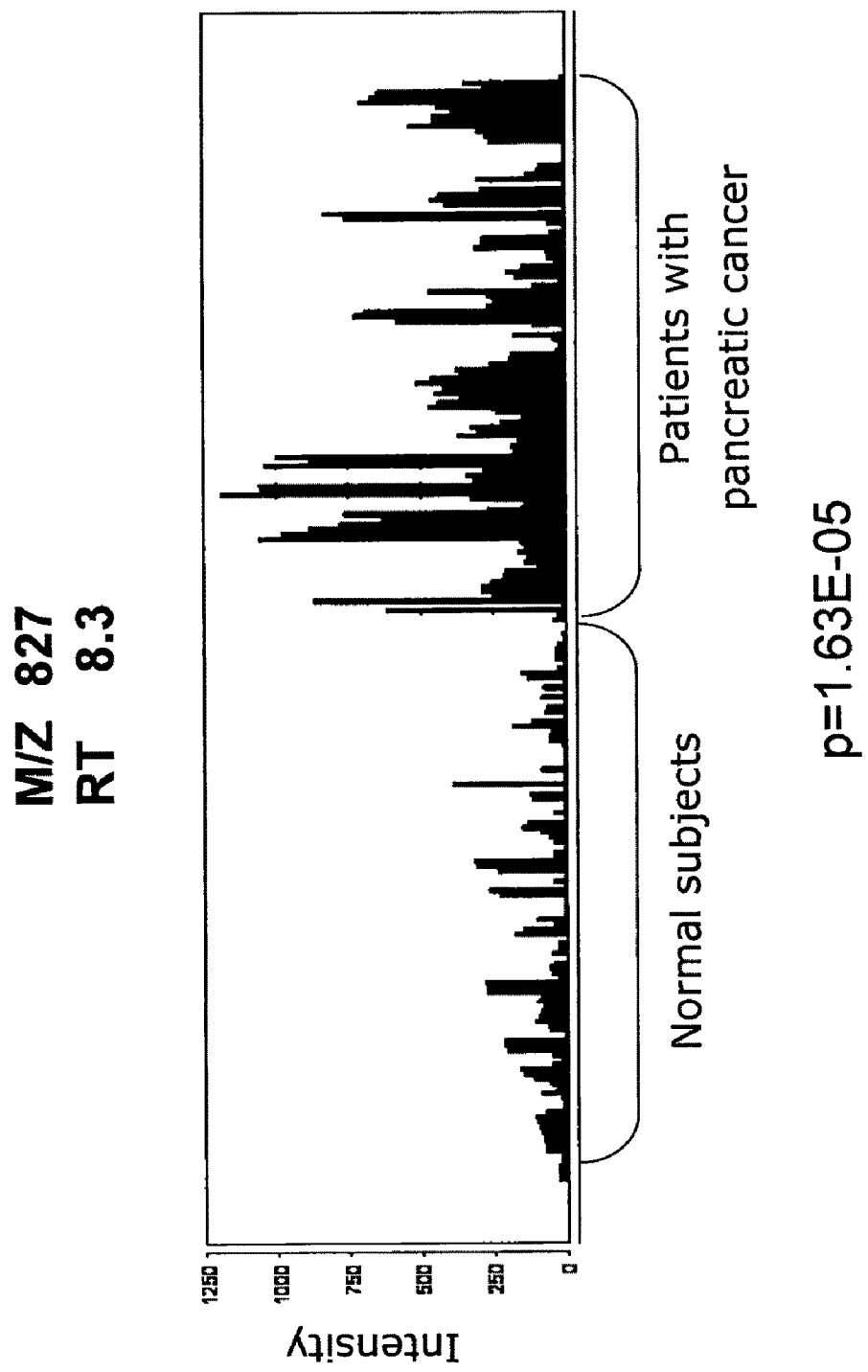
FIG. 1B is a histogram in which intensities of M/Z (mass-to-charge ratio) 827 of a glycoprotein fraction derived from a modified peptide in plasma samples and having a retention time (RT) of 8.3 minutes are compared among a plurality of the LC/MS data.
Figure 1C:
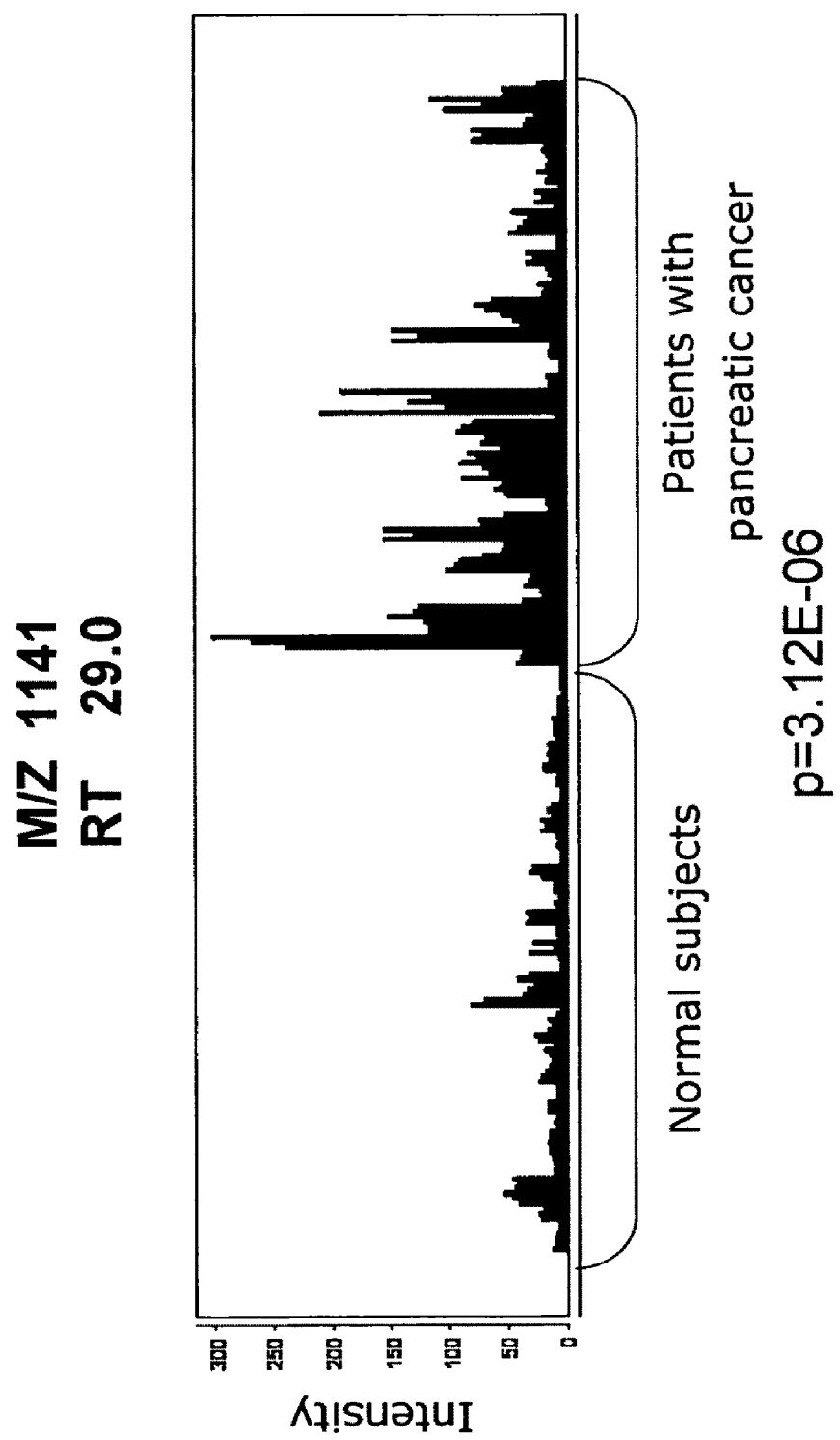
FIG. 1C is a histogram in which intensities of M/Z (mass-to-charge ratio) 1141 of a glycoprotein fraction derived from a modified peptide in plasma samples and having a retention time (RT) of 29.0 minutes are compared among a plurality of the LC/MS data.

FIG. 1A is a histogram in which the intensities of M/Z (mass-to-charge ratio) 552 at the retention time (RT) of 8.3 minutes were compared. FIG. 1B is a histogram in which the intensities of M/Z (mass-to-charge ratio) 827 at the retention time (RT) of 8.3 minutes were compared. FIG. 1C is a histogram in which the intensities of M/Z (mass-to-charge ratio) 1141 at the retention time (RT) of 29.0 minutes were compared. These peaks showed significant difference between patients with pancreatic cancer and normal subjects, as illustrated by the P value of U test shown under the histogram.

In addition, the discrimination ratio and the area under the ROC curve with these peaks were 83% and 0.85, 83% and 0.83, 76% and 0.82 in the order of M/Z 552, M/Z 827 and M/Z 1141, respectively, but in the same period having small dispersion of mass spectrometry 81% and 0.83, 89% and 0.92, 86% and 0.91, respectively.

Tandem mass spectrometry data were obtained on the three peaks described above, and the assay of peptide sequence including post-translational modification was carried out with the protein identification software (MASCOT). As a result, it has been found that both M/Z 552 and M/Z 827 at RT 8.3 minutes are derived from the sequence of ESSSHHPGIAEFPSR (SEQ ID NO: 5). It has also been found that M/Z 1141 at RT 29.0 minutes is derived from the sequence of TFPGFFSPMLGEFVSETESR (SEQ ID NO: 6). These amino acid sequences were both derived from fibrinogen. In addition, these peptides were post-translationally modified peptides 16 dalton higher than the molecular weight of the expected sequence.

With respect to an unmodified peptide corresponding to the post-translational modification, the difference of its expression was compared between pancreatic cancer patients and normal subjects by the 2DICAL method as described above. The result is illustrated in FIG. 2.

Figure 2A:
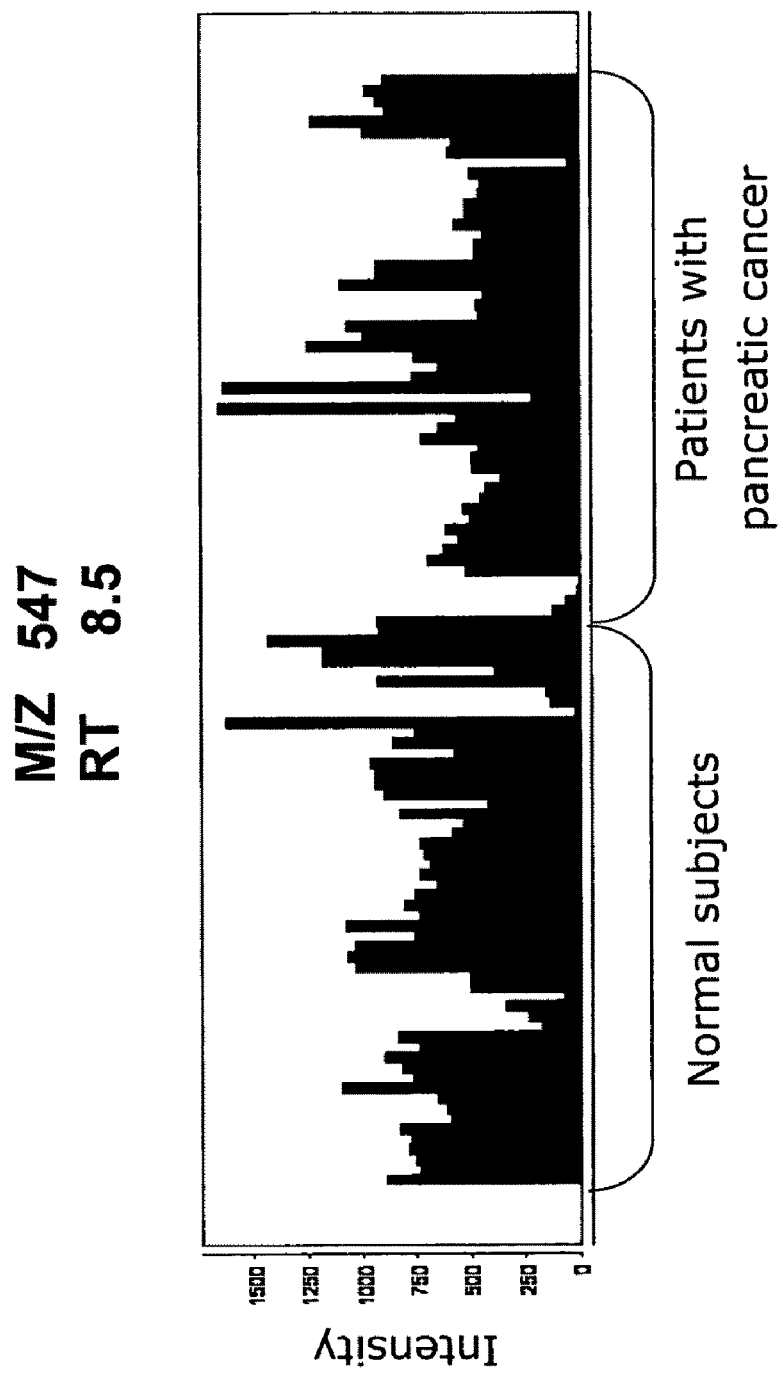
FIG. 2A is a histogram in which intensities of M/Z (mass-to-charge ratio) 547 of a glycoprotein fraction derived from an unmodified peptide in plasma samples and having a retention time (RT) of 8.5 minutes are compared among a plurality of the LC/MS data.
Figure 2B:
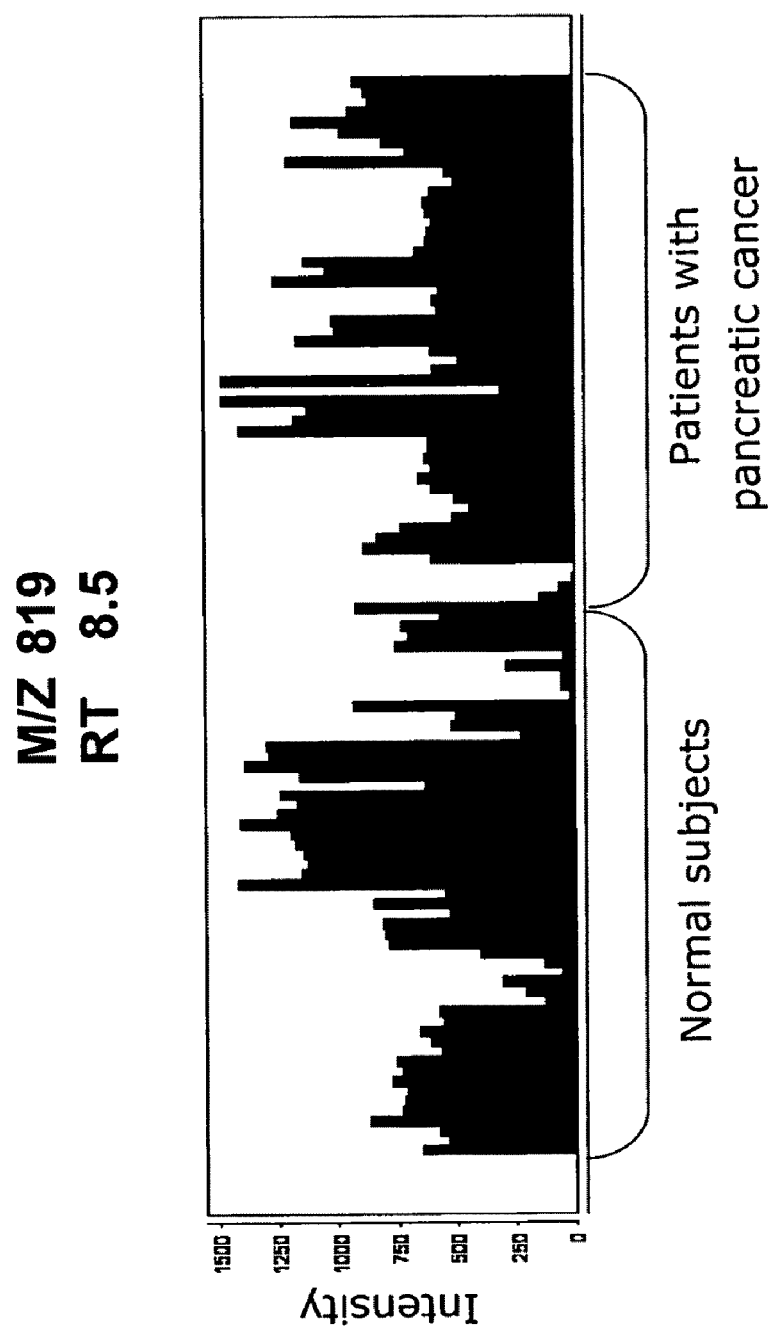
FIG. 2B is a histogram in which intensities of M/Z (mass-to-charge ratio) 819 of a glycoprotein fraction derived from a modified peptide in plasma samples and having a retention time (RT) of 8.5 minutes are compared among a plurality of the LC/MS data.
Figure 2C:
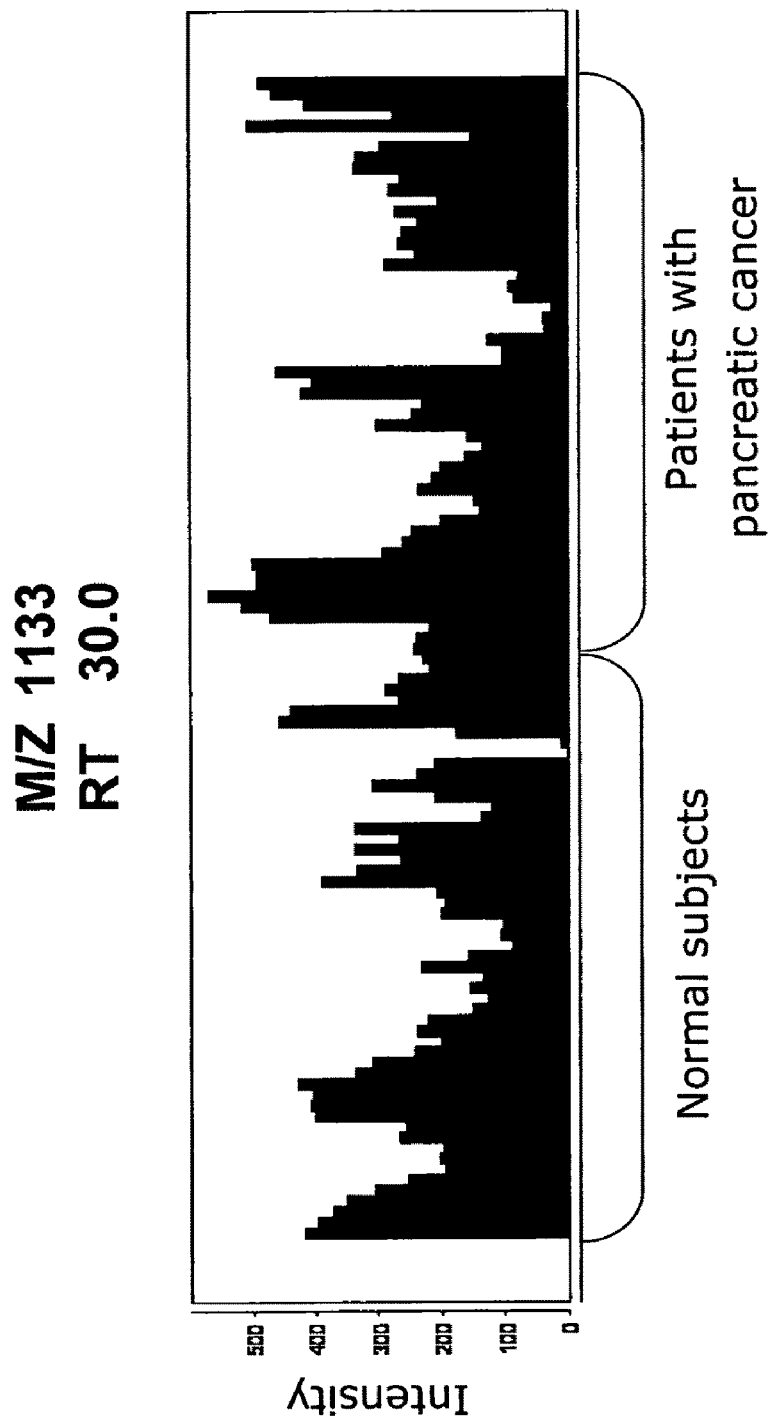
FIG. 2C is a histogram in which intensities of M/Z (mass-to-charge ratio) 1133 of a glycoprotein fraction derived from a modified peptide in plasma samples and having a retention time (RT) of 30.0 minutes are compared among a plurality of the LC/MS data.

FIG. 2A is a histogram in which the intensities of M/Z (mass-to-charge ratio) 547 at a retention time (RT) of 8.5 minutes were compared. FIG. 2B is a histogram in which the intensities of M/Z (mass-to-charge ratio) 819 at a retention time (RT) of 8.5 minutes were compared. FIG. 2C is a histogram in which the intensities of M/Z (mass-to-charge ratio) 1133 at a retention time (RT) of 30.0 minutes were compared. The intensities of these peaks derived from the unmodified peptides showed no difference between pancreatic cancer patients and normal subjects.

Next, the modification form of the two modified peptides described above was identified with an exact mass spectrometer Orbitrap (Thermo Fisher, San Jose, Calif.).

Figure 3:
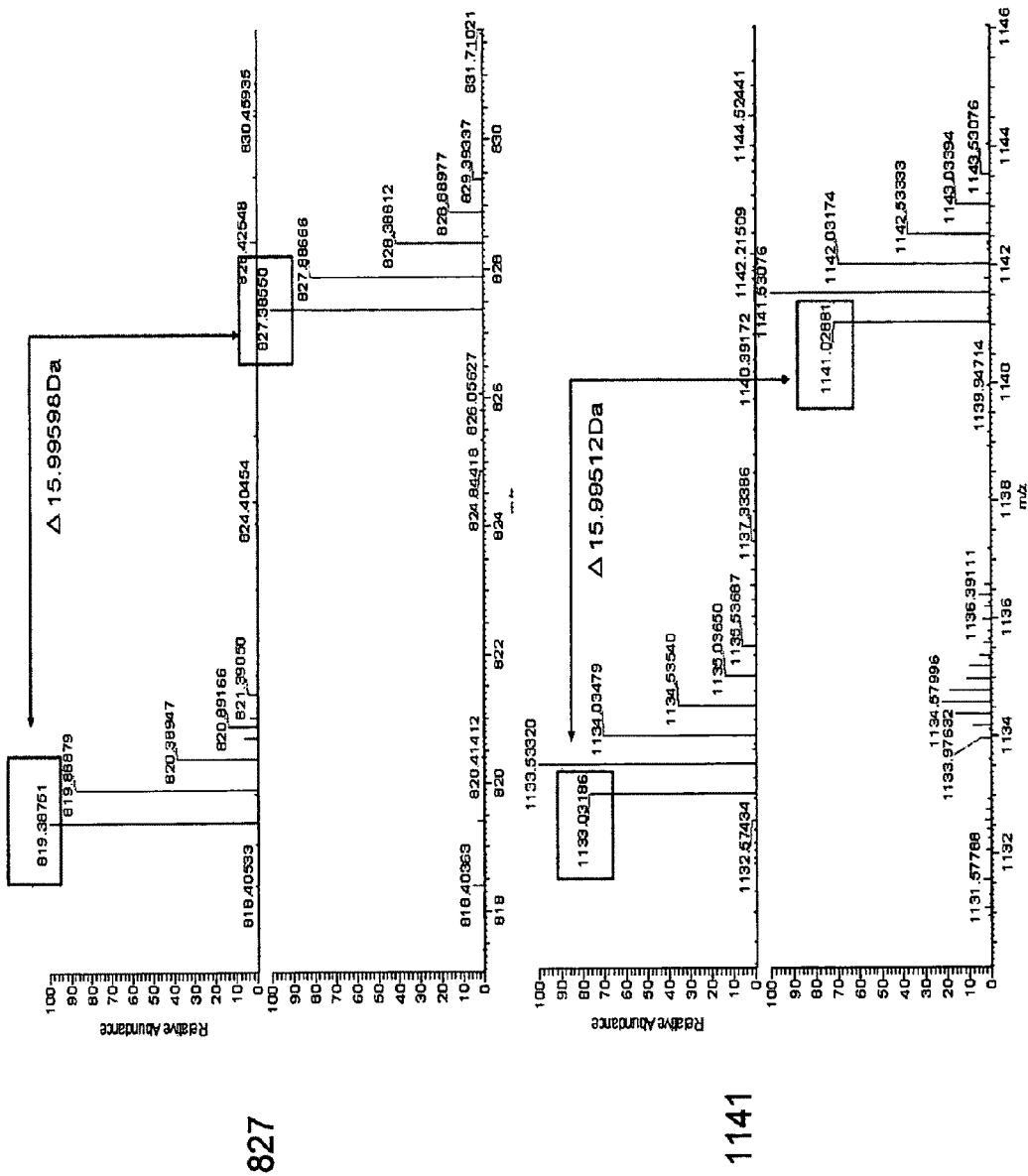
FIG. 3 illustrates the mass spectrograms in which the mass numbers of the modified peptide (827 m/z, 1141 m/z) and unmodified peptide (819 m/z, 1133 m/z) were calculated down to the third decimal place with Orbitrap.

The mass numbers of the modified peptide (827 m/z, 1141 m/z) and unmodified peptide (819 m/z, 1133 m/z) were calculated down to the third decimal place with the exact mass spectrometer Orbitrap. It has been confirmed that these peptides have a difference of mass numbers of 15.995 Da which corresponds to one oxygen atom (FIG. 3).

Figure 4:
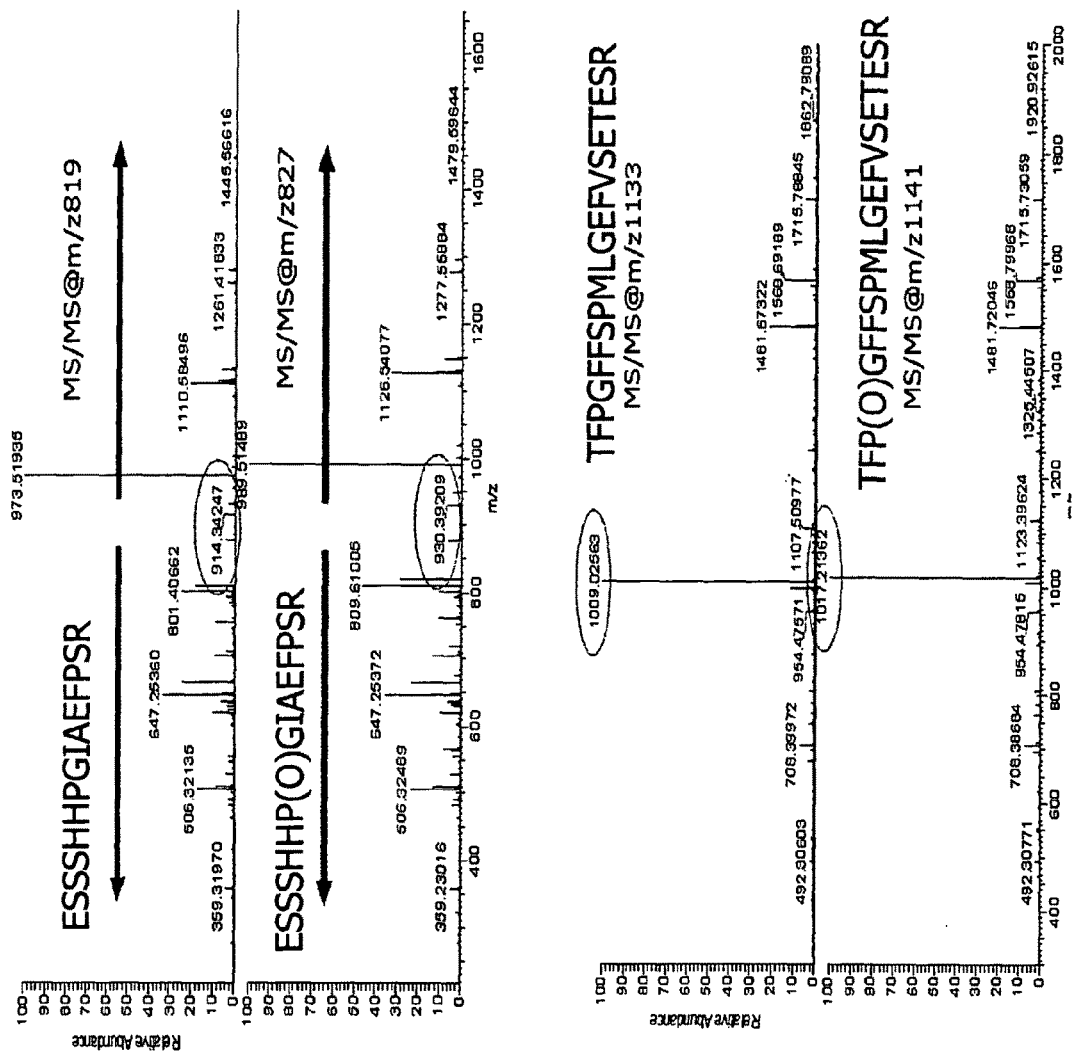
FIG. 4 illustrates the mass spectrograms which show the results of the determination by tandem mass spectrometry for a modified peptide (827 m/z, 1141 m/z) and an unmodified peptide (819 m/z, 1133 m/z).
Figure 5:
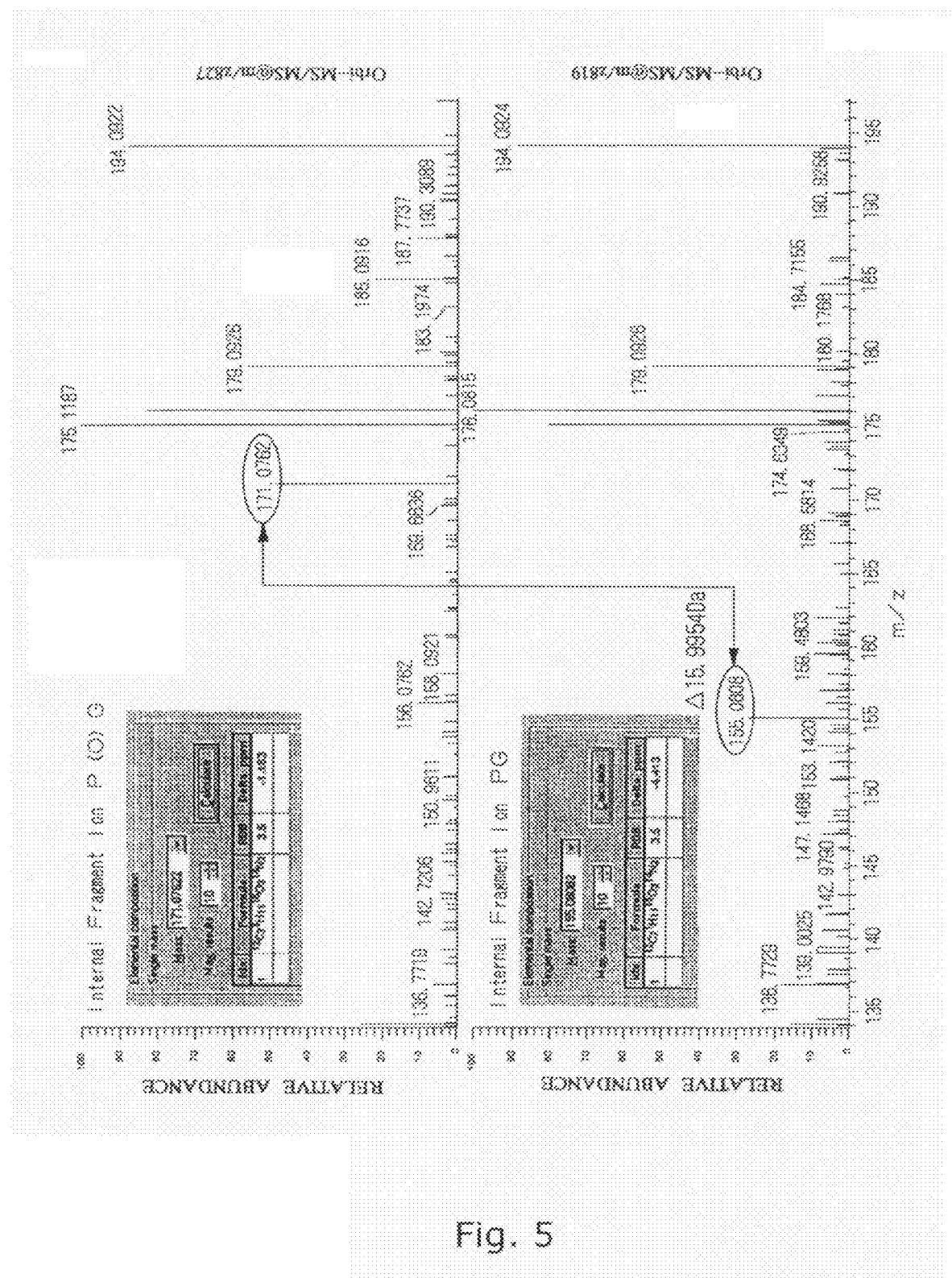
FIG. 5 illustrates the mass spectrograms which show the results of the determination of tandem mass spectrometry for a modified peptide (827 m/z) and an unmodified peptide (819 m/z).

The modified peptide (827 m/z, 1141 m/z) and the unmodified peptide (819 m/z, 1133 m/z) were subjected to tandem mass spectrometry analysis. The result is shown in FIG. 4. It has been confirmed from FIG. 4 that one oxygen atom difference between the fragments of these peptides is observed at the position of proline shown in the figure and thus the proline residue is oxidized.

Furthermore, tandem mass spectrometry analysis was performed with the exact mass spectrometer Orbitrap to confirm that the peptide showing 827 m/z is modified on the proline residue described above. As a result, it has been confirmed that the peptide residue 171.0762 m/z derived from the modified peptide and the peptide residue 155.0808 m/z derived from the unmodified peptide, of which the difference of the molecular weight is 15.995 Da, are unambiguously represented by the chemical formulas $C_7H_{11}O_3N_2$ and $C_7H_{11}O_2N_2$, respectively (FIG. 6). Peptide sequences having such structural formulas as described above are only represented by P(O)G and PG, and it has thus been confirmed that the peptide sequence ESSSHHP*GIAEFPSR is oxidized at the position of P*.

The invention claimed is:

1. An isolated modified α-fibrinogen protein containing an oxidized amino acid residue(s) or a fragment thereof containing said oxidized amino acid residue(s), wherein the amino acid residue(s) which is oxidized is one or more amino acid residues selected from the group consisting of
   (a) a proline residue corresponding to the proline residue at the position of 530 in SEQ ID NO: 2, and
   (b) a proline residue corresponding to the proline residue at the position of 565 in SEQ ID NO: 2.

2. The modified α-fibrinogen protein or a fragment thereof according to claim 1, wherein the oxidized amino acid residue has one additional oxygen atom as compared with the corresponding natural amino acid residue.

3. The modified α-fibrinogen protein or a fragment thereof according to claim 1, wherein the oxidized amino acid residue has one additional hydroxyl group as compared with the corresponding natural amino acid residue.

4. The modified α-fibrinogen protein or a fragment thereof according to claim 1, wherein both of the amino acid residues in (a) and (b) are oxidized.

5. The modified α-fibrinogen protein or a fragment thereof according to claim 1, wherein the α-fibrinogen protein comprises the residues at 20-644 positions in the amino acid sequence of SEQ ID NO: 2, in which either one or both of the proline residues at 530 and 565 positions are oxidized.

6. The modified α-fibrinogen protein or a fragment thereof according to claim 5, wherein both of the proline residue at the position of 530 and the proline residue at the position of 565 are oxidized.

7. The modified α-fibrinogen protein or a fragment thereof according to claim 1, wherein the α-fibrinogen protein comprises the residue at 20-866 positions in the amino acid sequence of SEQ ID NO: 4, and either one or both of the proline residues at positions 530 and 565 in the amino acid sequence are oxidized.

8. The modified α-fibrinogen protein or a fragment thereof according to claim 7, wherein both of the proline residue at the position of 530 and the proline residue at the position of 565 are oxidized.

9. The modified α-fibrinogen protein or a fragment thereof according to claim 1, wherein said fragment is an immunogenic fragment which can be used for the production of an antibody.

* * * * *

SEQUENCE LISTING

```
<160> NUMBER OF SEQ ID NOS: 6

<210> SEQ ID NO 1
<211> LENGTH: 2210
<212> TYPE: DNA
<213> ORGANISM: Homo sapiens
<220> FEATURE:
<221> NAME/KEY: CDS
<222> LOCATION: (59)..(1990)

<400> SEQUENCE: 1
agcaatcctt tctttcagct ggagtgctcc tcaggagcca gccccaccct tagaaaag       58 atg ttt tcc atg agg atc gtc tgc ctg gtc cta agt gtg gtg ggc aca      106
Met Phe Ser Met Arg Ile Val Cys Leu Val Leu Ser Val Val Gly Thr
1               5                   10                  15 gca tgg act gca gat agt ggt gaa ggt gac ttt cta gct gaa gga gga      154
Ala Trp Thr Ala Asp Ser Gly Glu Gly Asp Phe Leu Ala Glu Gly Gly
            20                  25                  30 ggc gtg cgt ggc cca agg gtt gtg gaa aga cat caa tct gcc tgc aaa      202
Gly Val Arg Gly Pro Arg Val Val Glu Arg His Gln Ser Ala Cys Lys
        35                  40                  45
```

-continued

| | |
|---|---|
| gat tca gac tgg ccc ttc tgc tct gat gaa gac tgg aac tac aaa tgc<br>Asp Ser Asp Trp Pro Phe Cys Ser Asp Glu Asp Trp Asn Tyr Lys Cys<br>50          55                  60 | 250 |
| cct tct ggc tgc agg atg aaa ggg ttg att gat gaa gtc aat caa gat<br>Pro Ser Gly Cys Arg Met Lys Gly Leu Ile Asp Glu Val Asn Gln Asp<br>65          70              75              80 | 298 |
| ttt aca aac aga ata aat aag ctc aaa aat tca cta ttt gaa tat cag<br>Phe Thr Asn Arg Ile Asn Lys Leu Lys Asn Ser Leu Phe Glu Tyr Gln<br>                85              90                  95 | 346 |
| aag aac aat aag gat tct cat tcg ttg acc act aat ata atg gaa att<br>Lys Asn Asn Lys Asp Ser His Ser Leu Thr Thr Asn Ile Met Glu Ile<br>            100              105              110 | 394 |
| ttg aga ggc gat ttt tcc tca gcc aat aac cgt gat aat acc tac aac<br>Leu Arg Gly Asp Phe Ser Ser Ala Asn Asn Arg Asp Asn Thr Tyr Asn<br>        115              120              125 | 442 |
| cga gtg tca gag gat ctg aga agc aga att gaa gtc ctg aag cgc aaa<br>Arg Val Ser Glu Asp Leu Arg Ser Arg Ile Glu Val Leu Lys Arg Lys<br>130              135              140 | 490 |
| gtc ata gaa aaa gta cag cat atc cag ctt ctg cag aaa aat gtt aga<br>Val Ile Glu Lys Val Gln His Ile Gln Leu Leu Gln Lys Asn Val Arg<br>145              150              155              160 | 538 |
| gct cag ttg gtt gat atg aaa cga ctg gag gtg gac att gat att aag<br>Ala Gln Leu Val Asp Met Lys Arg Leu Glu Val Asp Ile Asp Ile Lys<br>                165              170              175 | 586 |
| atc cga tct tgt cga ggg tca tgc agt agg gct tta gct cgt gaa gta<br>Ile Arg Ser Cys Arg Gly Ser Cys Ser Arg Ala Leu Ala Arg Glu Val<br>            180              185              190 | 634 |
| gat ctg aag gac tat gaa gat cag cag aag caa ctt gaa cag gtc att<br>Asp Leu Lys Asp Tyr Glu Asp Gln Gln Lys Gln Leu Glu Gln Val Ile<br>        195              200              205 | 682 |
| gcc aaa gac tta ctt ccc tct aga gat agg caa cac tta cca ctg ata<br>Ala Lys Asp Leu Leu Pro Ser Arg Asp Arg Gln His Leu Pro Leu Ile<br>210              215              220 | 730 |
| aaa atg aaa cca gtt cca gac ttg gtt ccc gga aat ttt aag agc cag<br>Lys Met Lys Pro Val Pro Asp Leu Val Pro Gly Asn Phe Lys Ser Gln<br>225              230              235              240 | 778 |
| ctt cag aag gta ccc cca gag tgg aag gca tta aca gac atg ccg cag<br>Leu Gln Lys Val Pro Pro Glu Trp Lys Ala Leu Thr Asp Met Pro Gln<br>                245              250              255 | 826 |
| atg aga atg gag tta gag aga cct ggt gga aat gag att act cga gga<br>Met Arg Met Glu Leu Glu Arg Pro Gly Gly Asn Glu Ile Thr Arg Gly<br>            260              265              270 | 874 |
| ggc tcc acc tct tat gga acc gga tca gag acg gaa agc ccc agg aac<br>Gly Ser Thr Ser Tyr Gly Thr Gly Ser Glu Thr Glu Ser Pro Arg Asn<br>        275              280              285 | 922 |
| cct agc agt gct gga agc tgg aac tct ggg agc tct gga cct gga agt<br>Pro Ser Ser Ala Gly Ser Trp Asn Ser Gly Ser Ser Gly Pro Gly Ser<br>290              295              300 | 970 |
| act gga aac cga aac cct ggg agc tct ggg act gga ggg act gca acc<br>Thr Gly Asn Arg Asn Pro Gly Ser Ser Gly Thr Gly Gly Thr Ala Thr<br>305              310              315              320 | 1018 |
| tgg aaa cct ggg agc tct gga cct gga agt act gga agc tgg aac tct<br>Trp Lys Pro Gly Ser Ser Gly Pro Gly Ser Thr Gly Ser Trp Asn Ser<br>                325              330              335 | 1066 |
| ggg agc tct gga act gga agt act gga aac caa aac cct ggg agc cct<br>Gly Ser Ser Gly Thr Gly Ser Thr Gly Asn Gln Asn Pro Gly Ser Pro<br>            340              345              350 | 1114 |
| aga cct ggt agt acc gga acc tgg aat cct ggc agc tct gaa cgc gga<br>Arg Pro Gly Ser Thr Gly Thr Trp Asn Pro Gly Ser Ser Glu Arg Gly<br>        355              360              365 | 1162 |

-continued

```
agt gct ggg cac tgg acc tct gag agc tct gta tct ggt agt act gga       1210
Ser Ala Gly His Trp Thr Ser Glu Ser Ser Val Ser Gly Ser Thr Gly
    370                 375                 380 caa tgg cac tct gaa tct gga agt ttt agg cca gat agc cca ggc tct       1258
Gln Trp His Ser Glu Ser Gly Ser Phe Arg Pro Asp Ser Pro Gly Ser
385                 390                 395                 400 ggg aac gcg agg cct aac aac cca gac tgg ggc aca ttt gaa gag gtg       1306
Gly Asn Ala Arg Pro Asn Asn Pro Asp Trp Gly Thr Phe Glu Glu Val
                405                 410                 415 tca gga aat gta agt cca ggg aca agg aga gag tac cac aca gaa aaa       1354
Ser Gly Asn Val Ser Pro Gly Thr Arg Arg Glu Tyr His Thr Glu Lys
            420                 425                 430 ctg gtc act tct aaa gga gat aaa gag ctc agg act ggt aaa gag aag       1402
Leu Val Thr Ser Lys Gly Asp Lys Glu Leu Arg Thr Gly Lys Glu Lys
        435                 440                 445 gtc acc tct ggt agc aca acc acc acg cgt cgt tca tgc tct aaa acc       1450
Val Thr Ser Gly Ser Thr Thr Thr Thr Arg Arg Ser Cys Ser Lys Thr
    450                 455                 460 gtt act aag act gtt att ggt cct gat ggt cac aaa gaa gtt acc aaa       1498
Val Thr Lys Thr Val Ile Gly Pro Asp Gly His Lys Glu Val Thr Lys
465                 470                 475                 480 gaa gtg gtg acc tcc gaa gat ggt tct gac tgt ccc gag gca atg gat       1546
Glu Val Val Thr Ser Glu Asp Gly Ser Asp Cys Pro Glu Ala Met Asp
                485                 490                 495 tta ggc aca ttg tct ggc ata ggt act ctg gat ggg ttc cgc cat agg       1594
Leu Gly Thr Leu Ser Gly Ile Gly Thr Leu Asp Gly Phe Arg His Arg
            500                 505                 510 cac cct gat gaa gct gcc ttc ttc gac act gcc tca act gga aaa aca       1642
His Pro Asp Glu Ala Ala Phe Phe Asp Thr Ala Ser Thr Gly Lys Thr
        515                 520                 525 ttc cca ggt ttc ttc tca cct atg tta gga gag ttt gtc agt gag act       1690
Phe Pro Gly Phe Phe Ser Pro Met Leu Gly Glu Phe Val Ser Glu Thr
    530                 535                 540 gag tct agg ggc tca gaa tct ggc atc ttc aca aat aca aag gaa tcc       1738
Glu Ser Arg Gly Ser Glu Ser Gly Ile Phe Thr Asn Thr Lys Glu Ser
545                 550                 555                 560 agt tct cat cac cct ggg ata gct gaa ttc cct tcc cgt ggt aaa tct       1786
Ser Ser His His Pro Gly Ile Ala Glu Phe Pro Ser Arg Gly Lys Ser
                565                 570                 575 tca agt tac agc aaa caa ttt act agt agc acg agt tac aac aga gga       1834
Ser Ser Tyr Ser Lys Gln Phe Thr Ser Ser Thr Ser Tyr Asn Arg Gly
            580                 585                 590 gac tcc aca ttt gaa agc aag agc tat aaa atg gca gat gag gcc gga       1882
Asp Ser Thr Phe Glu Ser Lys Ser Tyr Lys Met Ala Asp Glu Ala Gly
        595                 600                 605 agt gaa gcc gat cat gaa gga aca cat agc acc aag aga ggc cat gct       1930
Ser Glu Ala Asp His Glu Gly Thr His Ser Thr Lys Arg Gly His Ala
    610                 615                 620 aaa tct cgc cct gtc aga ggt atc cac act tct cct ttg ggg aag cct       1978
Lys Ser Arg Pro Val Arg Gly Ile His Thr Ser Pro Leu Gly Lys Pro
625                 630                 635                 640 tcc ctg tcc ccc tagactaagt taaatatttc tgcacagtgt tcccatggcc           2030
Ser Leu Ser Pro ccttgcattt ccttcttaac tctctgttac acgtcattga aactcacttt ttttggtctg     2090
tttttgtgct agactgtaag ttccttgggg gcagggcctt tgtctgtctc atctctgtat     2150
tcccaaatgc ctaacagtac agagccatga ctcaataaat acatgttaaa tggatgaatg     2210
```

<210> SEQ ID NO 2

<211> LENGTH: 644
<212> TYPE: PRT
<213> ORGANISM: Homo sapiens

<400> SEQUENCE: 2

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400
```

-continued

```
Gly Asn Ala Arg Pro Asn Asn Pro Asp Trp Gly Thr Phe Glu Glu Val
            405                 410                 415

Ser Gly Asn Val Ser Pro Gly Thr Arg Arg Glu Tyr His Thr Glu Lys
        420                 425                 430

Leu Val Thr Ser Lys Gly Asp Lys Glu Leu Arg Thr Gly Lys Glu Lys
    435                 440                 445

Val Thr Ser Gly Ser Thr Thr Thr Thr Arg Arg Ser Cys Ser Lys Thr
465                 470                 475                 480
(note: numbering as printed)

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 3
<211> LENGTH: 3655
<212> TYPE: DNA
<213> ORGANISM: Homo sapiens
<220> FEATURE:
<221> NAME/KEY: CDS
<222> LOCATION: (59)..(2656)

<400> SEQUENCE: 3
agcaatcctt tctttcagct ggagtgctcc tcaggagcca gccccaccct tagaaaag        58 atg ttt tcc atg agg atc gtc tgc ctg gtc cta agt gtg gtg ggc aca      106
Met Phe Ser Met Arg Ile Val Cys Leu Val Leu Ser Val Val Gly Thr
1               5                   10                  15 gca tgg act gca gat agt ggt gaa ggt gac ttt cta gct gaa gga gga      154
Ala Trp Thr Ala Asp Ser Gly Glu Gly Asp Phe Leu Ala Glu Gly Gly
            20                  25                  30 ggc gtg cgt ggc cca agg gtt gtg gaa aga cat caa tct gcc tgc aaa      202
Gly Val Arg Gly Pro Arg Val Val Glu Arg His Gln Ser Ala Cys Lys
        35                  40                  45 gat tca gac tgg ccc ttc tgc tct gat gaa gac tgg aac tac aaa tgc      250
Asp Ser Asp Trp Pro Phe Cys Ser Asp Glu Asp Trp Asn Tyr Lys Cys
    50                  55                  60 cct tct ggc tgc agg atg aaa ggg ttg att gat gaa gtc aat caa gat      298
Pro Ser Gly Cys Arg Met Lys Gly Leu Ile Asp Glu Val Asn Gln Asp
65                  70                  75                  80
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttt | aca | aac | aga | ata | aat | aag | ctc | aaa | aat | tca | cta | ttt | gaa | tat | cag | 346  |
| Phe | Thr | Asn | Arg | Ile | Asn | Lys | Leu | Lys | Asn | Ser | Leu | Phe | Glu | Tyr | Gln |      |
|     |     |     |     | 85  |     |     |     |     | 90  |     |     |     |     | 95  |     |      |
| aag | aac | aat | aag | gat | tct | cat | tcg | ttg | acc | act | aat | ata | atg | gaa | att | 394  |
| Lys | Asn | Asn | Lys | Asp | Ser | His | Ser | Leu | Thr | Thr | Asn | Ile | Met | Glu | Ile |      |
|     |     |     | 100 |     |     |     |     | 105 |     |     |     |     | 110 |     |     |      |
| ttg | aga | ggc | gat | ttt | tcc | tca | gcc | aat | aac | cgt | gat | aat | acc | tac | aac | 442  |
| Leu | Arg | Gly | Asp | Phe | Ser | Ser | Ala | Asn | Asn | Arg | Asp | Asn | Thr | Tyr | Asn |      |
|     |     | 115 |     |     |     |     | 120 |     |     |     |     | 125 |     |     |     |      |
| cga | gtg | tca | gag | gat | ctg | aga | agc | aga | att | gaa | gtc | ctg | aag | cgc | aaa | 490  |
| Arg | Val | Ser | Glu | Asp | Leu | Arg | Ser | Arg | Ile | Glu | Val | Leu | Lys | Arg | Lys |      |
|     | 130 |     |     |     |     | 135 |     |     |     |     | 140 |     |     |     |     |      |
| gtc | ata | gaa | aaa | gta | cag | cat | atc | cag | ctt | ctg | cag | aaa | aat | gtt | aga | 538  |
| Val | Ile | Glu | Lys | Val | Gln | His | Ile | Gln | Leu | Leu | Gln | Lys | Asn | Val | Arg |      |
| 145 |     |     |     |     | 150 |     |     |     |     | 155 |     |     |     |     | 160 |      |
| gct | cag | ttg | gtt | gat | atg | aaa | cga | ctg | gag | gtg | gac | att | gat | att | aag | 586  |
| Ala | Gln | Leu | Val | Asp | Met | Lys | Arg | Leu | Glu | Val | Asp | Ile | Asp | Ile | Lys |      |
|     |     |     |     | 165 |     |     |     |     | 170 |     |     |     |     | 175 |     |      |
| atc | cga | tct | tgt | cga | ggg | tca | tgc | agt | agg | gct | tta | gct | cgt | gaa | gta | 634  |
| Ile | Arg | Ser | Cys | Arg | Gly | Ser | Cys | Ser | Arg | Ala | Leu | Ala | Arg | Glu | Val |      |
|     |     |     | 180 |     |     |     |     | 185 |     |     |     |     | 190 |     |     |      |
| gat | ctg | aag | gac | tat | gaa | gat | cag | cag | aag | caa | ctt | gaa | cag | gtc | att | 682  |
| Asp | Leu | Lys | Asp | Tyr | Glu | Asp | Gln | Gln | Lys | Gln | Leu | Glu | Gln | Val | Ile |      |
|     | 195 |     |     |     |     | 200 |     |     |     |     | 205 |     |     |     |     |      |
| gcc | aaa | gac | tta | ctt | ccc | tct | aga | gat | agg | caa | cac | tta | cca | ctg | ata | 730  |
| Ala | Lys | Asp | Leu | Leu | Pro | Ser | Arg | Asp | Arg | Gln | His | Leu | Pro | Leu | Ile |      |
| 210 |     |     |     |     | 215 |     |     |     |     | 220 |     |     |     |     |     |      |
| aaa | atg | aaa | cca | gtt | cca | gac | ttg | gtt | ccc | gga | aat | ttt | aag | agc | cag | 778  |
| Lys | Met | Lys | Pro | Val | Pro | Asp | Leu | Val | Pro | Gly | Asn | Phe | Lys | Ser | Gln |      |
| 225 |     |     |     | 230 |     |     |     |     | 235 |     |     |     |     | 240 |     |      |
| ctt | cag | aag | gta | ccc | cca | gag | tgg | aag | gca | tta | aca | gac | atg | ccg | cag | 826  |
| Leu | Gln | Lys | Val | Pro | Pro | Glu | Trp | Lys | Ala | Leu | Thr | Asp | Met | Pro | Gln |      |
|     |     |     |     | 245 |     |     |     |     | 250 |     |     |     |     | 255 |     |      |
| atg | aga | atg | gag | tta | gag | aga | cct | ggt | gga | aat | gag | att | act | cga | gga | 874  |
| Met | Arg | Met | Glu | Leu | Glu | Arg | Pro | Gly | Gly | Asn | Glu | Ile | Thr | Arg | Gly |      |
|     |     | 260 |     |     |     |     | 265 |     |     |     |     | 270 |     |     |     |      |
| ggc | tcc | acc | tct | tat | gga | acc | gga | tca | gag | acg | gaa | agc | ccc | agg | aac | 922  |
| Gly | Ser | Thr | Ser | Tyr | Gly | Thr | Gly | Ser | Glu | Thr | Glu | Ser | Pro | Arg | Asn |      |
|     |     | 275 |     |     |     |     | 280 |     |     |     |     | 285 |     |     |     |      |
| cct | agc | agt | gct | gga | agc | tgg | aac | tct | ggg | agc | tct | gga | cct | gga | agt | 970  |
| Pro | Ser | Ser | Ala | Gly | Ser | Trp | Asn | Ser | Gly | Ser | Ser | Gly | Pro | Gly | Ser |      |
|     | 290 |     |     |     |     | 295 |     |     |     |     | 300 |     |     |     |     |      |
| act | gga | aac | cga | aac | cct | ggg | agc | tct | ggg | act | gga | ggg | act | gca | acc | 1018 |
| Thr | Gly | Asn | Arg | Asn | Pro | Gly | Ser | Ser | Gly | Thr | Gly | Gly | Thr | Ala | Thr |      |
| 305 |     |     |     | 310 |     |     |     |     | 315 |     |     |     |     | 320 |     |      |
| tgg | aaa | cct | ggg | agc | tct | gga | cct | gga | agt | act | gga | agc | tgg | aac | tct | 1066 |
| Trp | Lys | Pro | Gly | Ser | Ser | Gly | Pro | Gly | Ser | Thr | Gly | Ser | Trp | Asn | Ser |      |
|     |     |     |     | 325 |     |     |     |     | 330 |     |     |     |     | 335 |     |      |
| ggg | agc | tct | gga | act | gga | agt | act | gga | aac | caa | aac | cct | ggg | agc | cct | 1114 |
| Gly | Ser | Ser | Gly | Thr | Gly | Ser | Thr | Gly | Asn | Gln | Asn | Pro | Gly | Ser | Pro |      |
|     |     |     | 340 |     |     |     |     | 345 |     |     |     |     | 350 |     |     |      |
| aga | cct | ggt | agt | acc | gga | acc | tgg | aat | cct | ggc | agc | tct | gaa | cgc | gga | 1162 |
| Arg | Pro | Gly | Ser | Thr | Gly | Thr | Trp | Asn | Pro | Gly | Ser | Ser | Glu | Arg | Gly |      |
|     |     | 355 |     |     |     |     | 360 |     |     |     |     | 365 |     |     |     |      |
| agt | gct | ggg | cac | tgg | acc | tct | gag | agc | tct | gta | tct | ggt | agt | act | gga | 1210 |
| Ser | Ala | Gly | His | Trp | Thr | Ser | Glu | Ser | Ser | Val | Ser | Gly | Ser | Thr | Gly |      |
|     | 370 |     |     |     |     | 375 |     |     |     |     | 380 |     |     |     |     |      |
| caa | tgg | cac | tct | gaa | tct | gga | agt | ttt | agg | cca | gat | agc | cca | ggc | tct | 1258 |
| Gln | Trp | His | Ser | Glu | Ser | Gly | Ser | Phe | Arg | Pro | Asp | Ser | Pro | Gly | Ser |      |
| 385 |     |     |     |     | 390 |     |     |     |     | 395 |     |     |     |     | 400 |      |

| | |
|---|---|
| ggg aac gcg agg cct aac aac cca gac tgg ggc aca ttt gaa gag gtg<br>Gly Asn Ala Arg Pro Asn Asn Pro Asp Trp Gly Thr Phe Glu Glu Val<br>                405                    410                    415 | 1306 |
| tca gga aat gta agt cca ggg aca agg aga gag tac cac aca gaa aaa<br>Ser Gly Asn Val Ser Pro Gly Thr Arg Arg Glu Tyr His Thr Glu Lys<br>420                    425                    430 | 1354 |
| ctg gtc act tct aaa gga gat aaa gag ctc agg act ggt aaa gag aag<br>Leu Val Thr Ser Lys Gly Asp Lys Glu Leu Arg Thr Gly Lys Glu Lys<br>                435                    440                    445 | 1402 |
| gtc acc tct ggt agc aca acc acc acg cgt cgt tca tgc tct aaa acc<br>Val Thr Ser Gly Ser Thr Thr Thr Thr Arg Arg Ser Cys Ser Lys Thr<br>450                    455                    460 | 1450 |
| gtt act aag act gtt att ggt cct gat ggt cac aaa gaa gtt acc aaa<br>Val Thr Lys Thr Val Ile Gly Pro Asp Gly His Lys Glu Val Thr Lys<br>465                    470                    475                    480 | 1498 |
| gaa gtg gtg acc tcc gaa gat ggt tct gac tgt ccc gag gca atg gat<br>Glu Val Val Thr Ser Glu Asp Gly Ser Asp Cys Pro Glu Ala Met Asp<br>                          485                    490                    495 | 1546 |
| tta ggc aca ttg tct ggc ata ggt act ctg gat ggg ttc cgc cat agg<br>Leu Gly Thr Leu Ser Gly Ile Gly Thr Leu Asp Gly Phe Arg His Arg<br>                500                    505                    510 | 1594 |
| cac cct gat gaa gct gcc ttc ttc gac act gcc tca act gga aaa aca<br>His Pro Asp Glu Ala Ala Phe Phe Asp Thr Ala Ser Thr Gly Lys Thr<br>515                    520                    525 | 1642 |
| ttc cca ggt ttc ttc tca cct atg tta gga gag ttt gtc agt gag act<br>Phe Pro Gly Phe Phe Ser Pro Met Leu Gly Glu Phe Val Ser Glu Thr<br>530                    535                    540 | 1690 |
| gag tct agg ggc tca gaa tct ggc atc ttc aca aat aca aag gaa tcc<br>Glu Ser Arg Gly Ser Glu Ser Gly Ile Phe Thr Asn Thr Lys Glu Ser<br>545                    550                    555                    560 | 1738 |
| agt tct cat cac cct ggg ata gct gaa ttc cct tcc cgt ggt aaa tct<br>Ser Ser His His Pro Gly Ile Ala Glu Phe Pro Ser Arg Gly Lys Ser<br>                    565                    570                    575 | 1786 |
| tca agt tac agc aaa caa ttt act agt agc acg agt tac aac aga gga<br>Ser Ser Tyr Ser Lys Gln Phe Thr Ser Ser Thr Ser Tyr Asn Arg Gly<br>                580                    585                    590 | 1834 |
| gac tcc aca ttt gaa agc aag agc tat aaa atg gca gat gag gcc gga<br>Asp Ser Thr Phe Glu Ser Lys Ser Tyr Lys Met Ala Asp Glu Ala Gly<br>                595                    600                    605 | 1882 |
| agt gaa gcc gat cat gaa gga aca cat agc acc aag aga ggc cat gct<br>Ser Glu Ala Asp His Glu Gly Thr His Ser Thr Lys Arg Gly His Ala<br>610                    615                    620 | 1930 |
| aaa tct cgc cct gtc aga gac tgt gat gat gtc ctc caa aca cat cct<br>Lys Ser Arg Pro Val Arg Asp Cys Asp Asp Val Leu Gln Thr His Pro<br>625                    630                    635                    640 | 1978 |
| tca ggt acc caa agt ggc att ttc aat atc aag cta ccg gga tcc agt<br>Ser Gly Thr Gln Ser Gly Ile Phe Asn Ile Lys Leu Pro Gly Ser Ser<br>                    645                    650                    655 | 2026 |
| aag att ttt tct gtt tat tgc gat caa gag acc agt ttg gga gga tgg<br>Lys Ile Phe Ser Val Tyr Cys Asp Gln Glu Thr Ser Leu Gly Gly Trp<br>                660                    665                    670 | 2074 |
| ctt ttg atc cag caa aga atg gat gga tca ctg aat ttt aac cgg acc<br>Leu Leu Ile Gln Gln Arg Met Asp Gly Ser Leu Asn Phe Asn Arg Thr<br>675                    680                    685 | 2122 |
| tgg caa gac tac aag aga ggt ttc ggc agc ctg aat gac gag ggg gaa<br>Trp Gln Asp Tyr Lys Arg Gly Phe Gly Ser Leu Asn Asp Glu Gly Glu<br>690                    695                    700 | 2170 |
| gga gaa ttc tgg cta ggc aat gac tac ctc cac tta cta acc caa agg<br>Gly Glu Phe Trp Leu Gly Asn Asp Tyr Leu His Leu Leu Thr Gln Arg<br>705                    710                    715                    720 | 2218 |

```
ggc tct gtt ctt agg gtt gaa tta gag gac tgg gct ggg aat gaa gct    2266
Gly Ser Val Leu Arg Val Glu Leu Glu Asp Trp Ala Gly Asn Glu Ala
            725                 730                 735 tat gca gaa tat cac ttc cgg gta ggc tct gag gct gaa ggc tat gcc    2314
Tyr Ala Glu Tyr His Phe Arg Val Gly Ser Glu Ala Glu Gly Tyr Ala
        740                 745                 750 ctc caa gtc tcc tcc tat gaa ggc act gcg ggt gat gct ctg att gag    2362
Leu Gln Val Ser Ser Tyr Glu Gly Thr Ala Gly Asp Ala Leu Ile Glu
    755                 760                 765 ggt tcc gta gag gaa ggg gca gag tac acc tct cac aac aac atg cag    2410
Gly Ser Val Glu Glu Gly Ala Glu Tyr Thr Ser His Asn Asn Met Gln
770                 775                 780 ttc agc acc ttt gac agg gat gca gac cag tgg gaa gag aac tgt gca    2458
Phe Ser Thr Phe Asp Arg Asp Ala Asp Gln Trp Glu Glu Asn Cys Ala
785                 790                 795                 800 gaa gtc tat ggg gga ggc tgg tgg tat aat aac tgc caa gca gcc aat    2506
Glu Val Tyr Gly Gly Gly Trp Trp Tyr Asn Asn Cys Gln Ala Ala Asn
                805                 810                 815 ctc aat gga atc tac tac cct ggg ggc tcc tat gac cca agg aat aac    2554
Leu Asn Gly Ile Tyr Tyr Pro Gly Gly Ser Tyr Asp Pro Arg Asn Asn
            820                 825                 830 agt cct tat gag att gag aat gga gtg gtc tgg gtt tcc ttt aga ggg    2602
Ser Pro Tyr Glu Ile Glu Asn Gly Val Val Trp Val Ser Phe Arg Gly
        835                 840                 845 gca gat tat tcc ctc agg gct gtt cgc atg aaa att agg ccc ctt gtg    2650
Ala Asp Tyr Ser Leu Arg Ala Val Arg Met Lys Ile Arg Pro Leu Val
    850                 855                 860 acc caa taggctgaag aagtgggaat gggagcactc tgtcttcttt gctagagaag     2706
Thr Gln
865 tggagagaaa atacaaaagg taaagcagtt gagattctct acaacctaaa aaattcctag    2766 gtgctatttt cttatccttt gtactgtagc taaatgtacc tgagacatat tagtctttga    2826 aaaataaagt tatgtaaggt tttttttatc tttaaatagc tctgtgggtt ttaacatttt    2886 tataaagata taccaagggc cattcagtac atcaggaaag tggcagacag aagcttctct    2946 ctgcaacctt gaagactatt ggtttgagaa cttctcttcc cataccaccc aaaatcataa    3006 tgccattgga aagcaaaaag ttgttttatc catttgattt gaattgtttt aagccaatat    3066 tttaaggtaa aactcactga atctaaccat agctgacctt tgtagtagaa tttacaactt    3126 ataattacaa tgcacaattt ataattacaa tatgtattta tgtctttgc tatggagcaa     3186 atccaggaag gcaagagaaa cattctttcc taaatataaa tgaaaatcta tcctttaaac    3246 tcttccacta gacgttgtaa tgcacactta ttttttttccc aaggagtaac caatttcttt    3306 ctaaaacaca tttaaaattt taaaactatt tatgaatatt aaaaaaagac ataattcaca    3366 cattaataaa caatctccca agtattgatt taacttcatt tttctaataa tcataaacta    3426 tattctgtga catgctaatt attattaaat gtaagtcgtt agttcgaaag cctctcacta    3486 agtatgatct atgctatatt caaaattcaa cccatttact ttggtcaata tttgatctaa    3546 gttgcatctt taatcctggt ggtcttgcct tctgattttt aatttgtatc cttttctatt    3606 aagatatatt tgtcattttc tcttgaatat gtattaaaat atcccaagc                3655

<210> SEQ ID NO 4
<211> LENGTH: 866
<212> TYPE: PRT
<213> ORGANISM: Homo sapiens

<400> SEQUENCE: 4
```

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20              25                  30

Gly Val Arg Gly Pro Arg Val Glu Arg His Gln Ser Ala Cys Lys
        35              40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
                100                 105                 110

Leu Arg Gly Asp Phe Ser Ser Ala Asn Asn Arg Asp Asn Thr Tyr Asn
            115                 120                 125

Arg Val Ser Glu Asp Leu Arg Ser Arg Ile Glu Val Leu Lys Arg Lys
130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
    195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
            245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
            275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
            355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
```

```
                    420             425             430
Leu Val Thr Ser Lys Gly Asp Lys Glu Leu Arg Thr Gly Lys Glu Lys
            435                 440                 445

Val Thr Ser Gly Ser Thr Thr Thr Arg Arg Ser Cys Ser Lys Thr
        450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
        530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
        610                 615                 620

Lys Ser Arg Pro Val Arg Asp Cys Asp Asp Val Leu Gln Thr His Pro
625                 630                 635                 640

Ser Gly Thr Gln Ser Gly Ile Phe Asn Ile Lys Leu Pro Gly Ser Ser
                645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
        675                 680                 685

Trp Gln Asp Tyr Lys Arg Gly Phe Gly Ser Leu Asn Asp Glu Gly Glu
        690                 695                 700

Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
            725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
        755                 760                 765

Gly Ser Val Glu Glu Gly Ala Glu Tyr Thr Ser His Asn Asn Met Gln
        770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
            835                 840                 845
```

```
Ala Asp Tyr Ser Leu Arg Ala Val Arg Met Lys Ile Arg Pro Leu Val
        850                 855                 860

Thr Gln
865

<210> SEQ ID NO 5
<211> LENGTH: 15
<212> TYPE: PRT
<213> ORGANISM: Homo sapiens

<400> SEQUENCE: 5

Glu Ser Ser Ser His His Pro Gly Ile Ala Glu Phe Pro Ser Arg
1               5                   10                  15

<210> SEQ ID NO 6
<211> LENGTH: 20
<212> TYPE: PRT
<213> ORGANISM: Homo sapiens

<400> SEQUENCE: 6

Thr Phe Pro Gly Phe Phe Ser Pro Met Leu Gly Glu Phe Val Ser Glu
1               5                   10                  15

Thr Glu Ser Arg
            20
```